US00PP31205P2

(12) United States Plant Patent
Wood

(10) Patent No.: US PP31,205 P2
(45) Date of Patent: Dec. 10, 2019

(54) ***BERBERIS* PLANT NAMED 'AMERA'**

(50) Latin Name: *Berberis thunbergii*
Varietal Denomination: AMERA

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/350,427

(22) Filed: Nov. 15, 2018

(51) Int. Cl.
*A01H 5/00* (2018.01)
*A01H 6/00* (2018.01)

(52) U.S. Cl.
USPC ..... Plt./241

(58) Field of Classification Search
USPC ..... Plt./241
See application file for complete search history.

*Primary Examiner* — Susan McCormick Ewoldt
(74) *Attorney, Agent, or Firm* — C. A. Whealy

(57) ABSTRACT

A new and distinct cultivar of *Berberis* plant named 'AMERA', characterized by its relatively compact, upright, outwardly spreading and mounding plant habit; vigorous growth habit; freely branching habit; leaves that are initially yellow green in color with orange red-colored margins becoming darker yellow green in color with development; and good garden performance.

2 Drawing Sheets

Botanical designation: *Berberis thunbergii*.
Cultivar denomination: 'AMERA'.

CROSS-REFERENCED TO CLOSELY-RELATED APPLICATIONS

Title: *Berberis* Plant Named 'ARLENE'
Applicant: Timothy D. Wood
Ser. No. 16/350,428

BACKGROUND OF THE INVENTION

The present invention relates to a new and distinct cultivar of *Berberis* plant, commonly referred to as Barberry, botanically known as *Berberis thunbergii* and hereinafter referred to by the name 'AMERA'.

The new *Berberis* plant is a product of a planned breeding program conducted by the Inventor in Grand Haven, Mich. The objective of the breeding program was to develop new unique *Berberis* plants with unique plant form and attractive leaves.

The new *Berberis* plant originated from an open-pollination in 2005 of *Berberis thunbergii* 'Rose Glow', not patented, as the female, or seed parent and an unknown selection of *Berberis thunbergii* as the male, or pollen, parent. The new *Berberis* plant was discovered and selected by the Inventor during the summer of 2011 as a single plant within the progeny of the stated open-pollination in a controlled environment in Grand Haven, Mich.

Asexual reproduction of the new *Berberis* plant by softwood cuttings in a controlled greenhouse environment in Grand Haven, Mich. since the summer of 2011 has shown that the unique features of this new *Berberis* plant are stable and reproduced true to type in successive generations of asexual reproduction.

SUMMARY OF THE INVENTION

Plants of the new *Berberis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'AMERA'. These characteristics in combination distinguish 'AMERA' as a new and distinct *Berberis* plant:

1. Relatively compact, upright, outwardly spreading and mounding plant habit.
2. Vigorous growth habit.
3. Freely branching habit.
4. Leaves that are initially yellow green in color with orange red-colored margins becoming darker yellow green in color with development.
5. Good garden performance.

Plants of the new *Berberis* can be compared to plants of the female parent, 'Rose Glow'. Plants of the new *Berberis* differ primarily from plants of 'Rose Glow' in leaf color as plants of 'Rose Glow' have pink and burgundy bi-colored leaves.

Plants of the new *Berberis* can be compared to plants of *Berberis thunbergii* 'ARLENE', disclosed in U.S. Plant patent application Ser. No. 16/350,428. Plants of the new *Berberis* are more compact and more mounding than and not as outwardly spreading as plants of 'ARLENE'. In addition, plants of the new *Berberis* have solid-colored developed leaves whereas plants of 'ARLENE' have variegated leaves.

Plants of the new *Berberis* can also be compared to plants of the *Berberis thunbergii*, 'Koren', disclosed in U.S. Plant Pat. No. 24,818. In side-by-side comparisons, plants of the new *Berberis* differ primarily from plants of 'Koren' in the following characteristics:

1. Plants of the new *Berberis* are more compact than plants of 'Koren'.
2. Plants of the new *Berberis* and 'Koren' differ in developing leaf color as plants of the new *Berberis* have leaves that are initially yellow green in color with orange red-colored margins whereas plants of 'Koren' have leaves that do not have an orange red-colored margins.

3. Plants of the new *Berberis* and 'Koren' differ in developed leaf color as plants of the new *Berberis* have lighter yellow green-colored leaves than plants of 'Koren'.

BRIEF DESCRIPTION OF THE PHOTOGRAPHS

The accompanying colored photographs illustrate the overall appearance of the new *Berberis* plant showing the colors as true as it is reasonably possible to obtain in colored reproductions of this type. Colors in the photographs may differ slightly from the color values cited in the detailed botanical description which accurately describe the colors of the new *Berberis* plant.

The photograph on the first sheet is a side perspective view of a typical plant of 'AMERA' grown in a container.

The photograph on the second sheet is a close-up view of a typical flowering plant of 'AMERA'.

DETAILED BOTANICAL DESCRIPTION

The aforementioned photographs and following observations, measurements and values describe plants grown during the spring and summer in a polythelene-covered greenhouse in Grand Haven, Mich. and under cultural practices which closely approximate commercial *Berberis* production. During the production of the plants, day temperatures ranged from 18° C. to 27° C. and night temperatures ranged from 5° C. to 10° C. Plants were about two years old when the photographs and detailed description were taken. In the following detailed description, color references are made to The Royal Horticultural Society Colour Chart, 2015 Edition, except where general terms of ordinary dictionary significance are used.

Botanical classification: *Berberis thunbergii* 'AMERA'.

Parentage:

*Female, or seed, parent.*—*Berberis thunbergii* 'Rose Glow', not patented.

*Male, or pollen, parent*.—Unknown selection of *Berberis thunbergii*, not patented.

Propagation:

*Type*.—By softwood cuttings.

*Time to initiate roots, summer*.—About 20 days at temperatures ranging from 18° C. to 27° C.

*Time to produce a rooted young plant, summer*.—About three months at temperatures ranging from 18° C. to 27° C.

*Root description*.—Medium in thickness; fibrous; typically white to brown in color, actual color of the roots is dependent on substrate composition, water quality, fertilizer type and formulation, substrate temperature and physiological age of roots.

*Rooting habit*.—Freely branching; medium in density to dense.

Plant description:

*Plant form and growth habit*.—Perennial shrub; relatively compact, upright, outwardly spreading and mounding plant habit; rapid growth rate and vigorous growth habit; freely branching habit with about 30 to 40 lateral branches developing per plant.

*Plant height*.—About 23 cm.

*Plant diameter* (*area of spread*).—About 38.5 cm.

Lateral branch description:

*Length*.—About 18.5 cm.

*Diameter*.—About 1 mm.

*Internode length*.—About 1 cm.

*Aspect*.—About 45° from main stem axis.

*Strength*.—Strong, flexible.

*Texture*.—Smooth, glabrous.

*Color*.—Close to N200A.

*Thorns*.—Quantity: One thorn developing at each node. Length: About 5 mm. Width: About 0.5 mm. Color, developing stems: Close to 4D. Color, developed stems: Close to N199A.

Leaf description:

*Arrangement*.—Alternate or whorled; simple.

*Length*.—About 2.5 cm.

*Width*.—About 1.25 cm.

*Shape*.—Obovate to spatulate.

*Apex*.—Acute to obtuse.

*Base*.—Attenuate.

*Margin*.—Entire.

*Texture, upper and lower surfaces*.—Smooth, glabrous.

*Venation pattern*.—Pinnate.

*Color*.—Developing leaves, upper surface: Close to N144B; margin, close to 35B. Developing leaves, lower surface: Close to 145B. Fully expanded leaves, upper surface: Close to 144B; venation, close to 144B. Fully expanded leaves, lower surface: Close to 144C; venation, close to 144C.

*Petioles*.—Length: About 1 cm. Diameter: About 1 mm. Texture, upper and lower surfaces: Smooth, glabrous. Color, upper and lower surfaces: Close to 144C.

Flower description:

*Flower arrangement and habit*.—Flowers arranged in terminal umbellate fascicles of three to five flowers; flowers face outwardly to drooping; freely flowering habit with about 300 flowers developing per plant.

*Fragrance*.—None detected.

*Natural flowering season*.—Plants of the new Barberry flower during the spring in Grand Haven, Mich.

*Flower longevity*.—Flowers last about two weeks on the plant; flowers not persistent.

*Flower diameter*.—About 8 mm by 10 mm.

*Flower length* (*height*).—About 5 mm.

*Flower buds*.—Length: About 4 mm. Diameter: About 4 mm. Shape: Rounded, globose. Color: Close to 4B.

*Petals*.—Arrangement: About eleven in about two whorls. Length: About 5 mm. Width: About 3.5 mm. Shape: Obovate. Apex: Obtuse. Base: Cuneate. Margin: Entire. Texture, upper and lower surfaces: Smooth, glabrous. Color: When opening, upper and lower surfaces: Close to 4B. Fully opened, upper and lower surfaces: Close to 4B; color does not change with development.

*Sepals*.—To date, sepal development has not been observed on plants of the new *Berberis*.

*Peduncles*.—Length: About 9 mm. Diameter: Less than 1 mm. Aspect: Downward. Strength: Low, flexible. Texture: Smooth, glabrous. Color: Close to 47A.

*Reproductive organs*.—Stamens: Quantity: About six per flower. Filament length: About 1 mm. Filament color: Close to 137B. Anther length: About 1 mm. Anther shape: Globular. Anther color: Close to 12A. Pollen amount: Scarce. Pollen color: Close to 12A. Pistils: Quantity: One per flower. Pistil length: About 3 mm. Style length: About 3 mm. Style color: Close to 157B. Stigma color: Close to 157B. Ovary color: Close to 157B. Seeds and fruits: To date, seed and fruit development have not been observed on plants of the new *Berberis*.

Garden performance: Plants of the new Barberry have been observed to have good garden performance and to tolerate rain, wind and temperatures ranging from about −30° C. to about 38° C.

Pathogen & pest resistance: Plants of the new *Berberis* have not been observed to be resistant pathogens and pests common to *Berberis* plants.

It is claimed:

1. A new and distinct *Berberis* plant named 'AMERA' as illustrated and described.

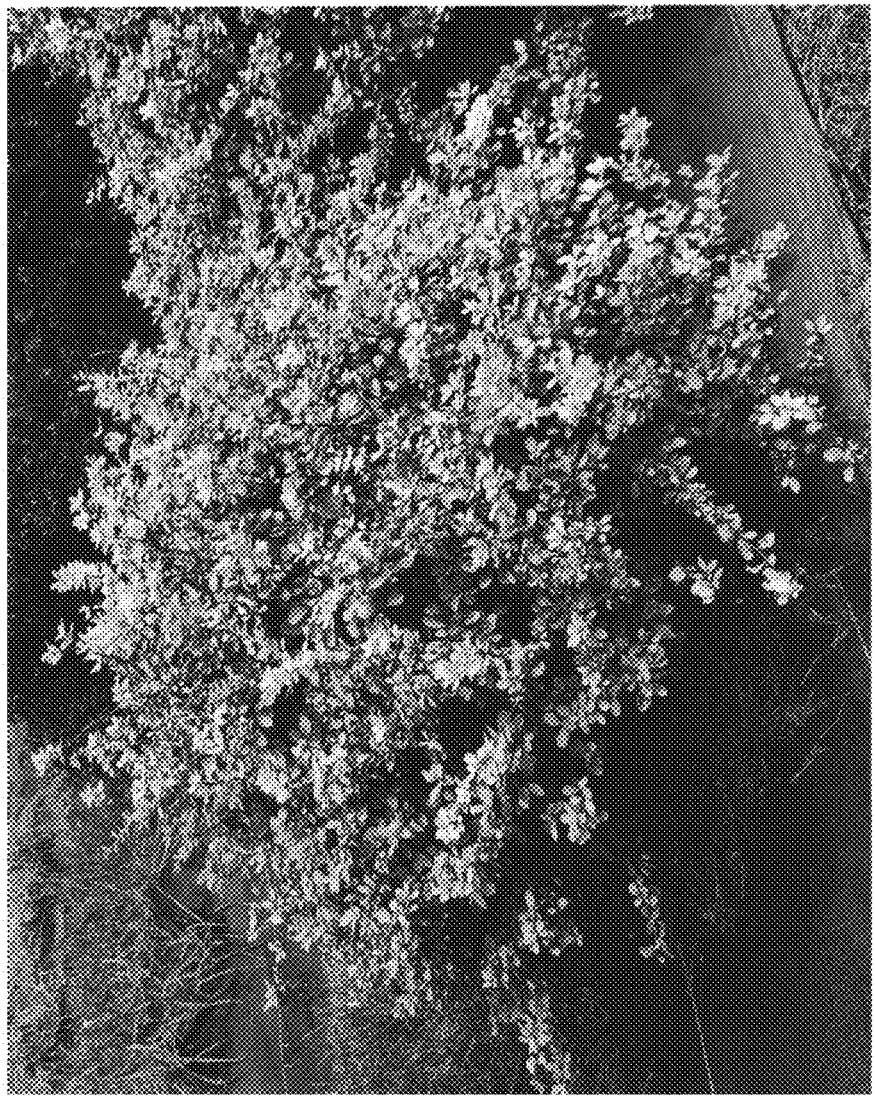

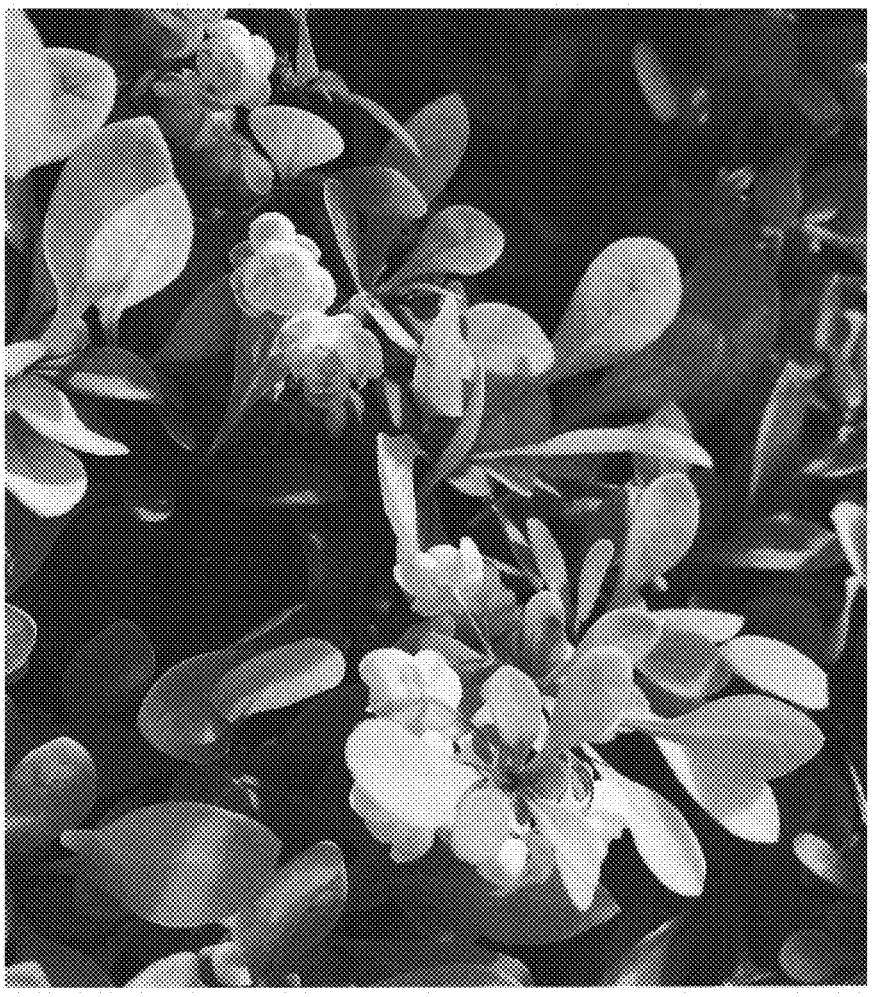

* * * * *